United States Patent [19]

Hamlin et al.

[11] Patent Number: 5,055,105
[45] Date of Patent: Oct. 8, 1991

[54] BONE DRILL BIT

[75] Inventors: Arthur H. Hamlin, Mendham, N.J.; Craig D. Morgan, Greenville, Del.

[73] Assignee: Bowen & Company, Ltd., Rockville, Md.

[21] Appl. No.: 419,776

[22] Filed: Oct. 11, 1989

[51] Int. Cl.⁵ ............................................. A61B 17/16
[52] U.S. Cl. ...................................... 606/80; 408/224; 408/228
[58] Field of Search ......................... 606/80, 179, 180; 408/228, 227, 224, 225, 117

[56] References Cited

U.S. PATENT DOCUMENTS

| | | |
|---|---|---|
| 195,181 | 9/1877 | Strohm . |
| 1,387,994 | 8/1921 | Lewis .................... 408/224 |
| 1,630,239 | 5/1924 | Binkley et al. . |
| 1,636,636 | 1/1927 | Humble . |
| 2,362,260 | 11/1944 | Foster .................... 408/224 |
| 2,623,552 | 12/1952 | Compton et al. .......... 408/227 X |
| 2,640,379 | 6/1953 | Graves ................... 408/228 |
| 2,667,795 | 2/1954 | Bowen ................... 408/224 |
| 3,006,223 | 8/1959 | Broussard . |
| 3,365,987 | 8/1965 | Heller et al. . |
| 3,923,413 | 12/1975 | Giles . |
| 4,541,423 | 9/1985 | Barber . |
| 4,612,922 | 9/1986 | Barber ................... 606/80 X |
| 4,646,738 | 3/1987 | Trott . |

OTHER PUBLICATIONS

"Bowen Arthroscopic Instruments", Brochure for a Suture Drill; Cat. No. 1275-0001.
Bowen & Company, Inc. "*Bankart Operation*", Brochure.

Primary Examiner—Michael H. Thaler
Attorney, Agent, or Firm—Larson & Taylor

[57] ABSTRACT

A bone drill bit for drilling a hole through bone, cartilage and/or other soft tissue, and the like includes an elongate cylindrical shaft having a pointed tip at one end and a shank at the other end which is adapted to be received in a surgical drilling apparatus. A plurality of small protuberances are provided around the cylindrical shaft adjacent the tip so that as the protuberances pass through the drilled bone a hole slightly larger than the shank is produced and thus the shank passes freely through the drilled hole. Preferably, the protuberances are diamond shaped and the pointed tip is pyramidal shaped. In addition, a suture holding device, such as an aperture or hook at the end of the shank, is provided for holding a suture to the shank as the shank passes through the drilled hole. A portion of the shank is cut away on either side of the suture holding device to provide clearance for the suture. Where the suture holding device is an aperture, this aperture is preferably countersunk at both ends.

10 Claims, 1 Drawing Sheet

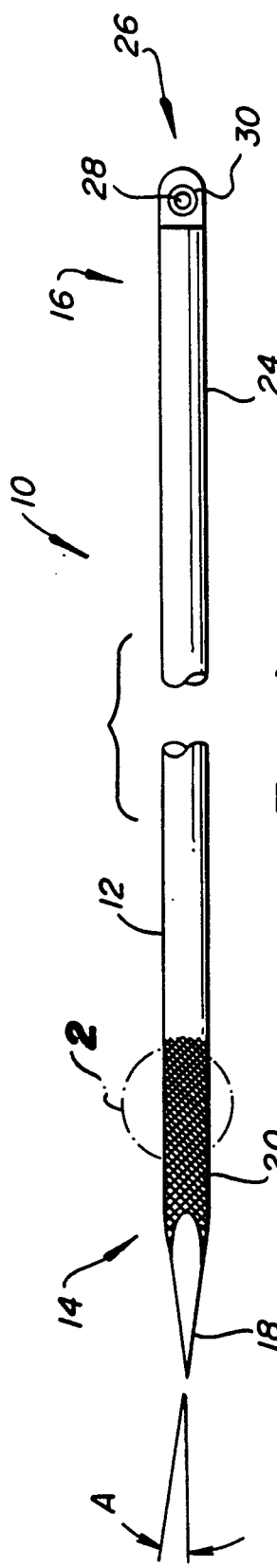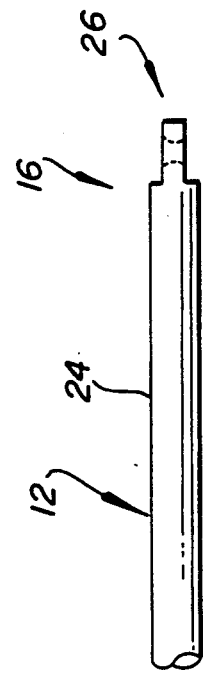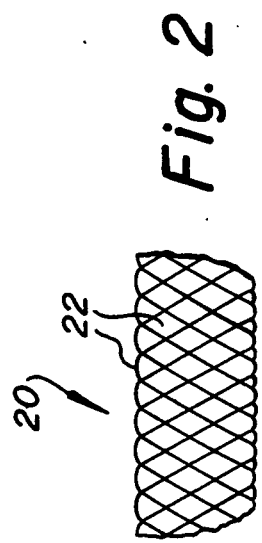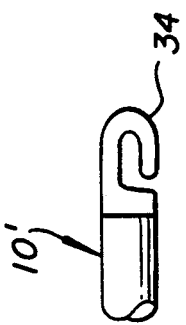

BONE DRILL BIT

FIELD OF THE INVENTION

The present invention relates generally to surgical drill bits for the drilling of bone, cartilage and the like, and more particularly to such a surgical bone drill bit which is additionally utilized for placing sutures through bone.

BACKGROUND OF THE INVENTION

In many various types of operations, it is desired to provide a hole through bone and/or soft tissue. Suturing may also be involved in such operations as when cartilage or other soft tissue is pulled away from associated bone. Thus, after holes are drilled in the soft tissue and bone, sutures are passed through the holes and used to hold the soft tissue or cartilage to the bone during healing.

Various drilling apparatus has been disclosed in the prior art. For example, in U.S. Pat. No. 4,541,423 (Barber) and U.S. Pat. No. 4,646,738 (Trott), rotary surgical tools used with arthroscopes and the like includes suitable drill bits for drilling holes.

Other drilling apparatuses of general interest and associated drilling bits are disclosed in the following U.S. Pat. Nos. 3,365,987 (Hallerdahl); 195,181 (Strohm); 3,923,413 (Giles); 3,006,223 (Broussard); 1,630,239 (Binkley, et al) and 1,636,636 (Humble).

There has also been disclosed in the prior art an angle drill attachment for a drill apparatus which is particularly adapted for use during a Bankart Operation. The drill bit provided with the angle drill attachment includes a hole at the end of the drill adjacent the cutting tip. Thus, after the hole is drilled to the bone, a suture can be threaded through this hole and pulled back through the bone as the drill bit is withdrawn from the bone.

SUMMARY OF THE INVENTION

In accordance with the present invention, a surgical bone drill bit for use with a suitable drilling apparatus includes an elongate cylindrical shaft having opposed end portions. At one end portion, a pointed tip is provided. At the other end portion, a shank is adapted to be received in a drilling apparatus. A plurality of small protuberances is provided around the cylindrical shaft only adjacent the tip. As the drill bit passes through the drilled bone, the protuberances provide a hole which is slightly larger than the shank so that the shank then easily passes through the drilled hole.

In accordance with a preferred embodiment of the present invention, the small protuberances are diamond shaped and suitably formed by a knurling operation. The pointed tip is also pyramidal shaped and has four sides.

A suture holding means is also preferably provided on the shank for holding a suture to the shank as the shank passes through the drilled hole. The suture holding means is conveniently an aperture at the end of the shank distal from the tip. A portion of the shank adjacent the aperture is partially cut away and the aperture is preferably countersunk on each side thereof. Alternatively, a hook at the end of the shank distal from the tip can be provided.

It is an advantage of the present invention that an efficient, easy-to-use bone drill bit is provided.

It is also an advantage of the present invention that the hole drilled by the bone drill bit is enlarged slightly by protuberances provided thereon.

It is a further advantage of the present invention that the enlarged hole provided by the bone drill bit protuberances together with a holding means on the end of the bone drill bit allow a suture to be easily pulled through the drilled hole with the bone drill bit.

Other features and advantages of the present invention are stated in or are apparent from a detailed description of a presently preferred embodiment of the invention found hereinbelow.

BRIEF DESCRIPTION OF THE DRAWINGS

FIG. 1 is a side view of a bone drill bit according to the present invention.

FIG. 2 is an enlarged view of a portion of the bone drill bit depicted in FIG. 1 identified by the broken circle numbered 2.

FIG. 3 is a side view of a portion of the drill bit depicted in FIG. 1 which has been rotated 90.

FIG. 4 is a side view of a portion of an alternative drill bit according to the present invention.

DETAILED DESCRIPTION OF THE PREFERRED EMBODIMENT

With reference now to the drawings in which like numerals represent like elements, a bone drill bit 10 according to the present invention is depicted in FIG. 1. Bone drill bit 10 is suitably about 12" long and is formed from an elongate cylindrical shaft 12. Cylindrical shaft 12 has a proximal end portion 14 and a distal end portion 16. At proximal end portion 14, cylindrical shaft 12 is formed into a pointed tip 18. Conveniently, pointed tip 18 is formed into a pyramidal shape by machining four flat sides at an angle A of about 8 to the shaft axis of cylindrical shaft 12.

Located adjacent pointed tip 18 is a knurled portion 20 of cylindrical shaft 12. It should be appreciated that knurled portion 20 is located only along a small portion of cylindrical shaft 12 adjacent pointed tip 18. It should also be appreciated that in the knurling process, a plurality of small protuberances 22 are created in the knurling process so that the distance between protuberances 22 on either side of cylindrical shaft 12 is slightly greater than the diameter of cylindrical shaft 12. As shown, protuberances 22 are diamond shaped with a 30° pattern although 45° or other patterns and even a straight knurl would be possible.

Distal end portion 16 of cylindrical shaft 12 includes a shank 24 which is adapted to be received in a chuck of a suitable bone drilling apparatus (not shown). Conveniently, shank 24 is simply a portion of cylindrical shaft 12 which is received in a suitable chuck which tightens around such a cylindrical shape.

Distal end portion 16 also includes a suture holding means 26. Suture holding means 26 in its preferred embodiment takes the form of a simple aperture 28 provided in distal end portion 16. Aperture 28 preferably includes countersinks 30 to make it easier to thread a suture through aperture 28. In addition, portions of distal end portion 16 have been cut away on each side of aperture 28 before countersinks 30 are formed to provide clearance for a suture extending through each side of aperture 28 as distal end portion 16 is pulled through the hole drilled by bone drill bit 10. A convenient size for aperture 28 is 0.040" diameter.

Besides circular aperture 28 depicted, suture holding means 26 could also be elongated (more like a slot) or a hook 34 as depicted in FIG. 4 on drill bit 10'. Obviously, it would generally be easier to attach a suture to hook 34 than to thread aperture 28, but it would also be easier for the suture to accidentally be freed from hook 34.

In operation, bone drill bit 10 functions in the following manner. Initially, shank 24 of bone drill bit 10 is received in a suitable chuck or the like of a bone drilling apparatus. Thereafter, pointed tip 18 is used to start a hole in the bone to be drilled as bone drill bit 10 is rotated by the drilling apparatus. The hole through the bone is completed as knurled portion 20 also passes through the bone. It should be appreciated that knurled portion 20 causes the drilled hole to have a slightly larger diameter than the diameter of the unknurled portion of cylindrical shaft 12. Then, assuming a suture is to be passed through the hole drilled, bone drill bit 10 is removed from the chuck of the drilling apparatus and a suture is simply threaded through aperture 28. Knurled portion 20 of bone drill bit 10 is then grasped by the user and bone drill bit 10 is pulled through the hole together with the suture in suture holding means 26. This process is repeated for additional holes as needed.

It should be appreciated by those of ordinary skill in the art that instead of a 0.040" diameter aperture 28, a 0.1040" slot could be substituted therefor. In addition, the present invention is useable for other than surgical uses.

While the present invention has been described with respect to an exemplary embodiment thereof, it will be understood by those of ordinary skill in the art that variations and modifications can be effected within the scope and spirit of the invention.

We claim:

1. A bone drill bit for use with a drilling apparatus for drilling a hole through a bone comprising:
   an elongate cylindrical shaft having opposed end portions, one said end portion forming a shank which is adapted to be received in the drilling apparatus;
   a pointed tip at the other said end portion; and
   a plurality of small protuberances provided around and projecting beyond a diameter of said cylindrical shaft beginning at said tip and extending for a short distance along said shaft such that as said protuberances pass through the drilled bone a hole slightly larger than the diameter of said shank is produced and thus a remainder of said shank passes freely through the drilled hole.

2. A bone drill bit as claimed in claim 1 wherein said protuberances are diamond shaped.

3. A bone drill bit as claimed in claim 2 wherein said pointed tip is pyramidal shaped.

4. A bone drill bit as claimed in claim 3 wherein said suture holding means is an aperture at an end of said shank distal from said tip.

5. A bone drill bit as claimed in claim 4 wherein said aperture is countersink at both ends thereof.

6. A bone drill bit as claimed in claim 5 wherein said end of said shank is partially cut away on each side of said aperture.

7. A bone drill bit as claimed in claim 3 wherein said suture holding means is a hook at an end of said shank distal from said tip.

8. A bone drill bit as claimed in claim 1 wherein said suture holding means is an aperture at an end of said shank distal from said tip.

9. A bone drill bit as claimed in claim 8 wherein said aperture is countersunk at both ends thereof.

10. A bone drill bit as claimed in claim 1 wherein said suture holding means is a hook at an end of said shank distal from said tip.

* * * * *